United States Patent
Kojima et al.

(10) Patent No.: US 7,149,565 B2
(45) Date of Patent: *Dec. 12, 2006

(54) TOMOGRAM CREATING METHOD

(75) Inventors: Shinichi Kojima, Hitachi (JP); Kikuo Umegaki, Hitachinaka (JP); Yuuichirou Ueno, Hitachi (JP); Kensuke Amemiya, Hitachinaka (JP); Hiroshi Kitaguchi, Naka (JP); Takashi Okazaki, Hitachinaka (JP); Kazuma Yokoi, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/673,496

(22) Filed: Sep. 30, 2003

(65) Prior Publication Data

US 2004/0062345 A1    Apr. 1, 2004

Related U.S. Application Data

(63) Continuation of application No. 10/253,489, filed on Sep. 25, 2002.

(30) Foreign Application Priority Data

Feb. 13, 2002   (JP) ............................. 2002-34783

(51) Int. Cl.
*A61B 6/00*    (2006.01)
(52) U.S. Cl. ................. 600/427; 600/431; 600/436; 250/363.03; 378/4
(58) Field of Classification Search ............ 600/411, 600/427, 431, 436; 378/4, 21; 250/363.03
See application file for complete search history.

(56) References Cited

U.S. PATENT DOCUMENTS 5,871,013 A     2/1999   Wainer et al.
6,490,476 B1 *  12/2002  Townsend et al. .......... 600/427
6,841,782 B1 *  1/2005   Balan et al. ........... 250/363.02

FOREIGN PATENT DOCUMENTS

DE    196 21 540    1/1997
JP    3022773       1/1991

OTHER PUBLICATIONS

L.A. Shepp, et al., "Reconstructing Interior Head Tissue From X-Ray Transmissions", Bell Laboratories, pp. 228-236.

(Continued)

*Primary Examiner*—Ruth S. Smith
(74) *Attorney, Agent, or Firm*—Dickstein Shapiro LLP

(57) ABSTRACT

An X-ray CT examination using a radiation examining apparatus corresponding to an X-ray CT is effected on an unbreathed examinee. A tomogram creating apparatus creates a first tomogram, based on an X-ray detect signal outputted from a corresponding radiation detector of the radiation examining apparatus. An X-ray CT examination and a PET examination using a radiation examining apparatus are effected on the breathed examinee. The tomogram creating apparatus creates a second tomogram, based on an X-ray detect signal outputted from a corresponding radiation detector of the radiation examining apparatus and creates a third tomogram, based on a γ-ray detect signal outputted from the corresponding radiation detector. Correction information is created based on the first and second tomograms. The third tomogram is corrected using the correction information. Therefore, the corrected third tomogram can be obtained which is not affected by a swing produced with breathing.

6 Claims, 9 Drawing Sheets

OTHER PUBLICATIONS

D. Rueckert, et al., Nonrigid Registration Using Free-Form Deformations: Application to Breast MR Images, IEEE Transactions on Medical Imaging, vol. 18, No. 8, Aug. 1999, pp. 712-721.

Michel Defrise, et al., "Exact and Approxmiate Rebinning Algorithms for 3-D PET Data", IEEE Transactions on Medical Imaging, vol. 16, No. 2, Apr. 1997, pp. 145-158.

* cited by examiner

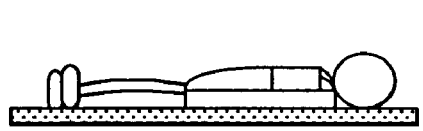
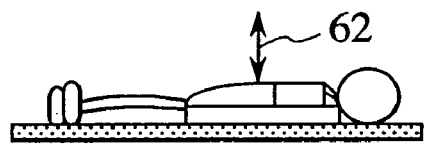
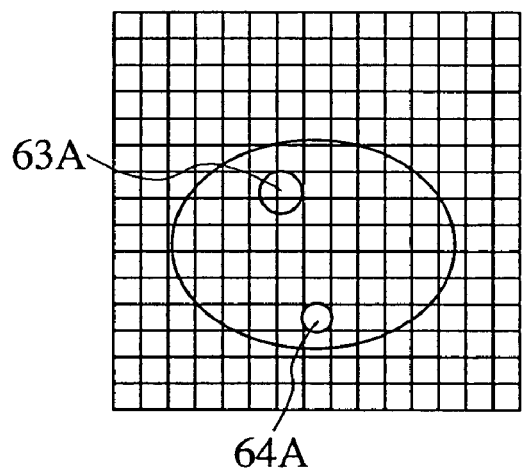
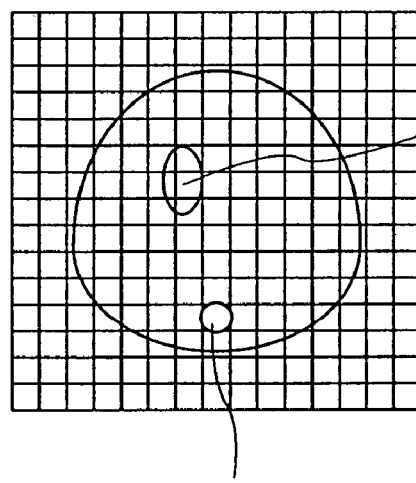

TOMOGRAM CREATING METHOD

CROSS REFERENCE TO RELATED APPLICATIONS

This application is a continuation of application Ser. No. 10/253,489, filed on Sep. 25, 2002, which claims priority to Japanese Patent Application Serial No. 2002-034783, filed on Feb. 13, 2002, which is hereby incorporated by reference.

BACKGROUND OF THE INVENTION

The present invention relates to a tomogram creating device, a tomogram creating method and a radiation examining apparatus, and particularly to a tomogram creating device, a tomogram creating method and a radiation examining apparatus suitable for application to the creation of tomograms by positron emission CT (Position Emission Computed Tomography (hereinafter called "PET")) or the creation of tomograms by X-ray CT and single photon emission CT (Single Photon Emission Computed Tomography (hereinafter called "SPECT")).

As a technology for non-invasively imaging functions, forms in a body of an object to be examined or an examinee, there is known an examination using radiation. As typical ones of radiation examining apparatuses, there are known X-ray CT, MRI, PET, SPECT, etc.

The X-ray CT is a method of irradiating an object to be examined or an examinee with radiation emitted from an X-ray source and imaging the form of the body from transmission of the radiation in the body of the examinee. By detecting the intensity of X rays transmitted through the body by a radiation detecting element, a linear attenuation coefficient between the X-ray source and the radiation detecting element is obtained. The linear attenuation coefficient of each voxel is determined by a Filtered Back Projection Method or the like described in IEEE Transaction on Nuclear Science Vol. NS-21, pp 228–229. The determined value is converted into a CT value. A radiation source well used in the X-ray CT is about 80 keV or so.

The PET examination is a method of administrating a radioactive medical agent (hereinafter called "PET medical agent") containing positron emission nuclear species ($^{15}O$, $^{13}N$, $^{11}C$, $^{18}F$. ect.), and a substance (marker substance) having the property of concentrating on a specific cell in a body to an examinee corresponding to a body to be examined, and examining in which region the PET medical agent is consumed or used up in excess. Positrons emitted from the PET medical agent are coupled to electrons in the vicinity thereof to yield positron extinction, thus radiating a pair of γ rays (hereinafter called "γ-ray pair") having an energy of 511 keV. Since the respective γ rays of each γ-ray pair are radiated in directions directly opposite to each other, in between which two of radiation detectors the positrons are emitted, is found out if the γ rays of each γ-ray pair are detected by the radiation detectors. By detecting a large number of the γ-ray pairs, locations where the PET medical agent is much consumed, can be found out. When a PET medical agent using sugar or glucose as the marker substance is administered to an examinee, for example, a cancer acutely varied in carbohydrate metabolism can be found. Incidentally, the resultant data is converted into data of each voxel in a body by a method such as the aforementioned Filtered Back Projection Method.

In the SPECT examination, a radioactive medical agent (SPECT medical agent) containing single photon emission nuclear species ($^{99}Tc$, $^{67}Ga$, $^{201}Tl$, etc.) is administered to an examinee and γ rays emitted from the nuclear species are detected by a γ-ray detector. The energy of the γ rays emitted from the single photo emission nuclear species is a few 100 keV or so. Since the single γ ray is emitted in the case of the SPECT, the angel at which it is launched into the corresponding radiation detector, cannot be obtained. Thus, a collimator is used to detect only γ rays incident from a specific angle by means of the corresponding radiation detector, whereby angular information is obtained. Even in the case of the SPECT, the resultant data is converted into data of each voxel in a body by a method such as the Filtered Back Projection Method or the like. Incidentally, a transmission image is often imaged even in the case of the SPECT. The half-life of the single photon emission nuclear species used in the SPECT is longer than the half-life of the positron emission nuclear species used in the PET and ranges from six hours to three days.

Nuclear medicine examinations of the PET and SPECT need examination time intervals ranging from a few minutes to several tens of minutes, whereas MRI and X-ray CT examinations are completed in a few seconds to several tens of seconds. Therefore, the MRI examination and X-ray CT examination can be carried out in a state in which an examinee is being unbreathed. Since, however, the PET and SPECT or the like are not capable of performing examinations in the unbreathed state, the examinations are performed in a state in which the examinee is being breathed. Therefore, there is adopted a method of reducing artifacts (displacements of an image incident to the motion of a body) produced due to the motion of the body by means of a method such as the collection of only data in a specific state according to breath synchronization.

Japanese Patent No. 3022773 proposes detecting a chest position with breathing of an examinee by means of a position sensor, correcting a SPECT image, based on a signal detected by the sensor and correcting image blurring produced with breath movements.

Since the examination time becomes long in the method of eliminating the breath artifacts according to the breath synchronization, the same method is inefficient. The correcting method described in Japanese Patent No. 3022773 is capable of shortening an examination time interval. Since, however, the correcting method described in Japanese Patent No. 3022773 detects the chest position (breath-based swing) of the examinee by means of the position sensor, the swing of each individual region in the body of the examinee cannot be accurately grasped. Thus, a tomogram good in accuracy cannot be obtained depending on the correction of Japanese Patent No. 3022773, and the accuracy of a diagnosis effected on a region on which a radioactive medical agent is concentrated in the body, cannot be improved.

SUMMARY OF THE INVENTION

An object of the present invention is to provide a tomogram creating device, a tomogram creating method and a radiation examining apparatus capable of improving the accuracy of a diagnosis on a region on which a radioactive medical agent concentrates.

A feature of the present invention to achieve the above-described object resides in that correction information of a tomogram is created based on data about a first structural tomogram created based on a first radiation detect signal detected in an unbreathed state of a body to be examined with respect to radiation transmitted through the body, and data about a second structural tomogram created based on a second radiation detect signal detected in a breathed state of the body with respect to radiation transmitted through the body, and data about a functional tomogram is created based on a third radiation detect signal detected in the breathed state of the body with respect to radiation emitted from the body due to a radioactive medical agent, and the correction information.

According to the feature referred to above, the corrections using the respective data about the first structural tomogram obtained based on the first radiation detect signal in the unbreathed state and the second structural tomogram obtained based on the second radiation detect signal in the breathed state make it possible to obtain a tomogram for radiation emitted traceable from a body to be examined, in which the influence of a breath-based swing is less reduced. Therefore, the accuracy of a diagnosis on a region on which a radioactive medical agent is concentrated, is improved.

BRIEF DESCRIPTION OF THE DRAWINGS

Other objects and advantages of the invention will become apparent from the following description of embodiments with reference to the accompanying drawings in which:

FIG. 8 shows tomograms obtained based on respective X-ray detect signals detected by radiation examining apparatuses 1 and 40 in the first embodiment, wherein FIG. 8A is an explanatory view showing a first X-ray CT image obtained based on an X-ray detect signal obtained by an X-ray CT examination in an unbreathed state, which has been executed using the radiation examining apparatus 40, and FIG. 8B is an explanatory view showing a second X-ray CT image obtained based on an X-ray detect signal obtained by an X-ray CT examination in a breathed state, which has been executed using the radiation examining apparatus 1;

FIG. 11 shows tomograms obtained based on respective X-ray detect signals detected by radiation examining apparatuses 1 and 40 in the third embodiment, wherein

DESCRIPTION OF THE PREFERRED EMBODIMENTS

First Embodiment

Figure 1:
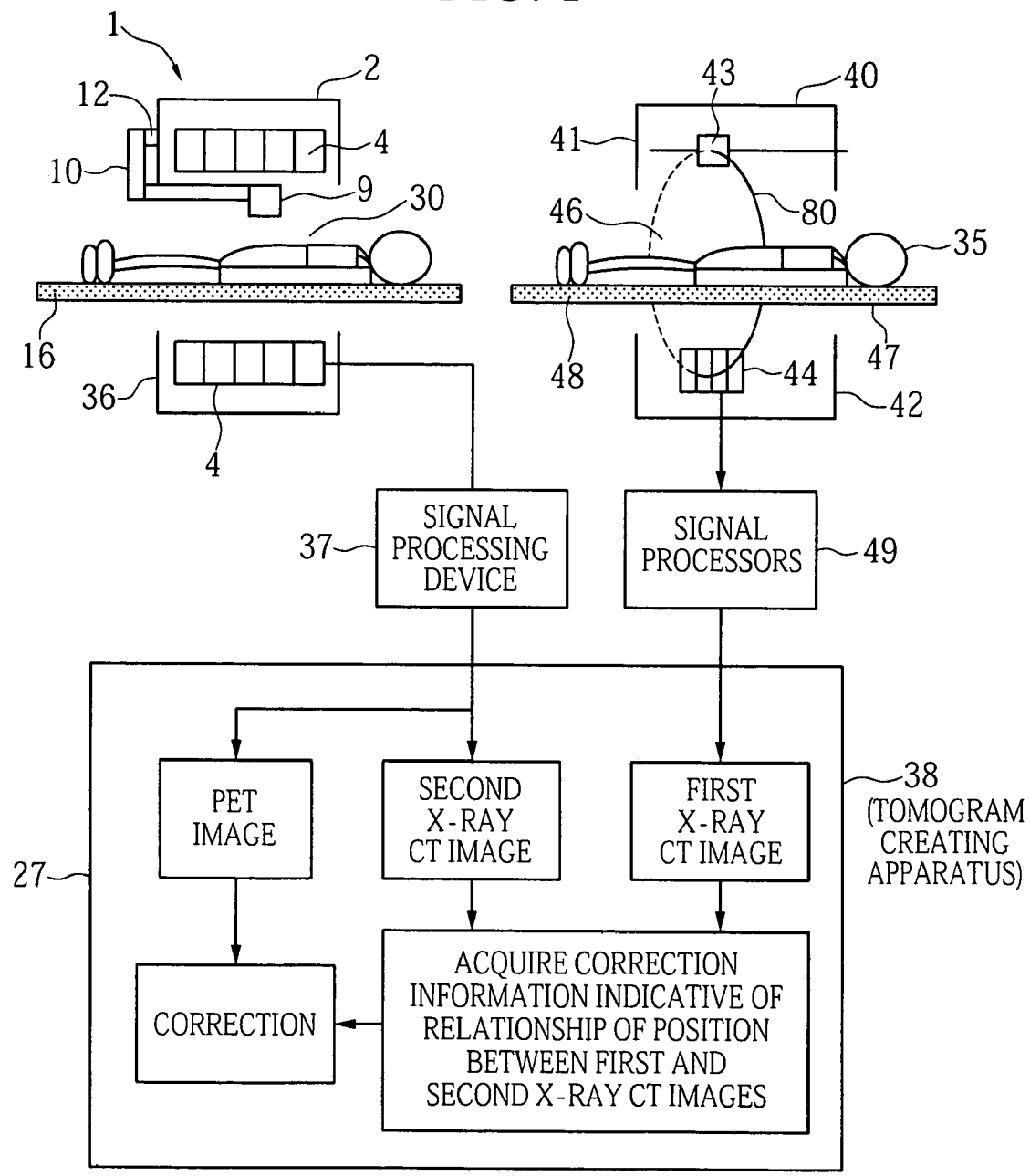
FIG. 1 is a configurational view of a radiation examining system used in a tomogram creating method of a first embodiment, which shows a preferred embodiment of the present invention.

A first radiation examining apparatus 1 and a second radiation examining apparatus 40 are used in a tomogram creating method showing one preferred embodiment of the present invention as shown in FIG. 1. The radiation examining apparatus 1 is capable of carrying out both a PET examination and an X-ray CT examination (corresponding to a behavior or action for detecting X-rays radiated from an X-ray source and transmitted through a body of an object to be examined or an examinee, by means of a radiation detector) and a PET examination (detecting γ rays radiated from the body due to a radioactive medical agent for PET by means of a radiation detector). The radiation examining apparatus 40 is an X-ray CT for executing an X-ray CT examination.

A schematic structure of the radiation examining apparatus 40 will be explained below using FIG. 1. The radiation examining apparatus 40 is provided with an imaging device 41 and an examinee holding device 47. The imaging device 41 includes an X-ray source 43 and a plurality of radiation detectors 44 provided within a casing 42. The imaging device 41 forms a through hole or opening portion 46 corresponding to an observation region in which an object to be examined or an examinee 35 is inserted for its examination. The X-ray source 43 and the plurality of radiation detectors 44 are placed in opposite directions at an angle of nearly 180° with the through hole section 46 interposed therebetween. They are coupled to each other by a coupling member 80. The X-ray source 43 and the plurality of radiation detectors 44 are able to turn around the through hole section 46 along a guide (not shown) provided within the casing 42. The examinee holding device 47 has a bed 48 positioned at an upper end of a support member (not shown) and mounted to the support member so as to be movable in its longitudinal direction. Signal processing devices or processors 49 are provided every radiation detectors 44 and connected to their corresponding radiation detectors 44. Each of the signal processing devices 49 is connected to a computer 27 of a tomogram creating apparatus 38.

Figure 2:
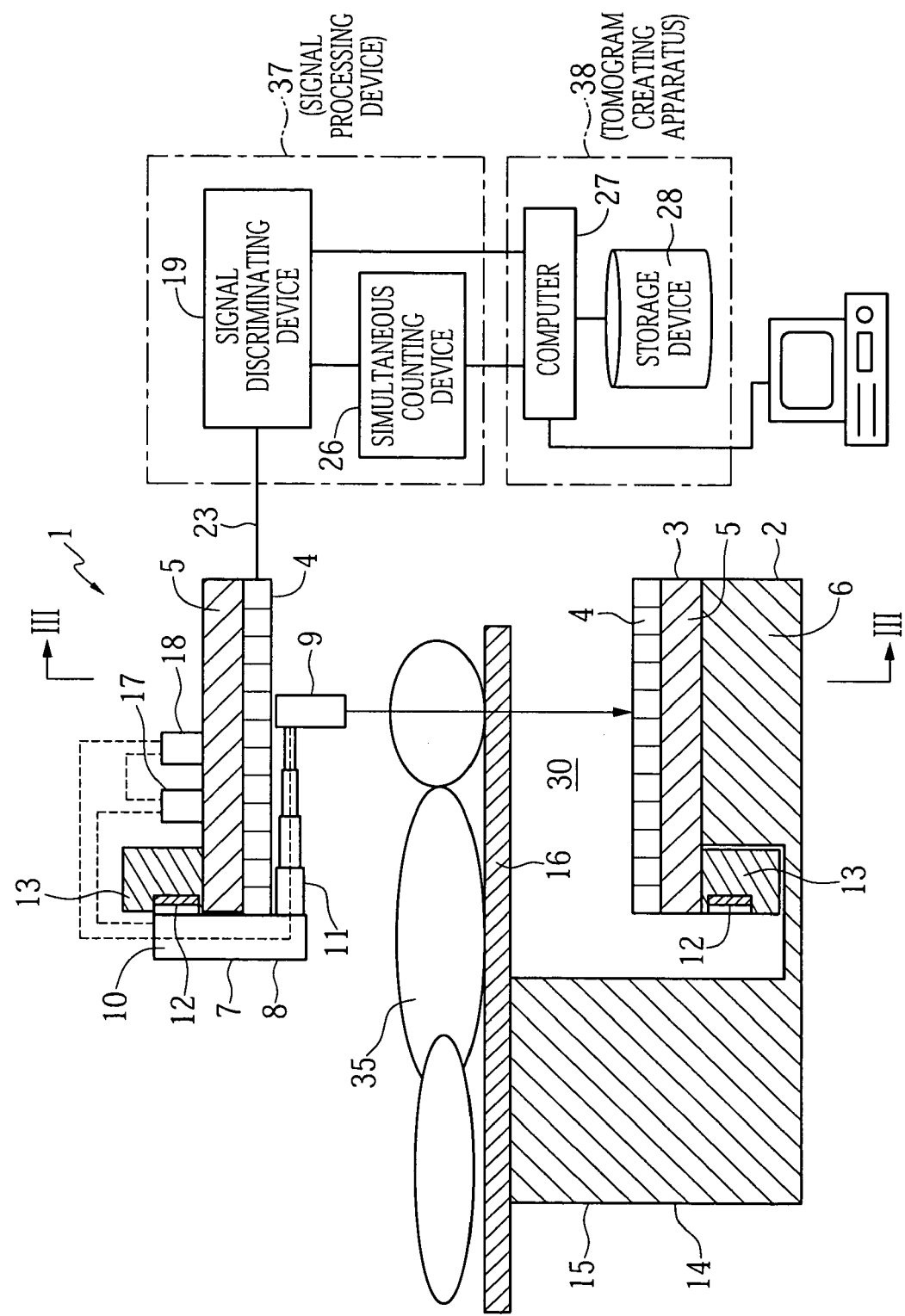
FIG. 2 is a detailed configurational view of a radiation examining apparatus 1 of FIG. 1.
Figure 3:
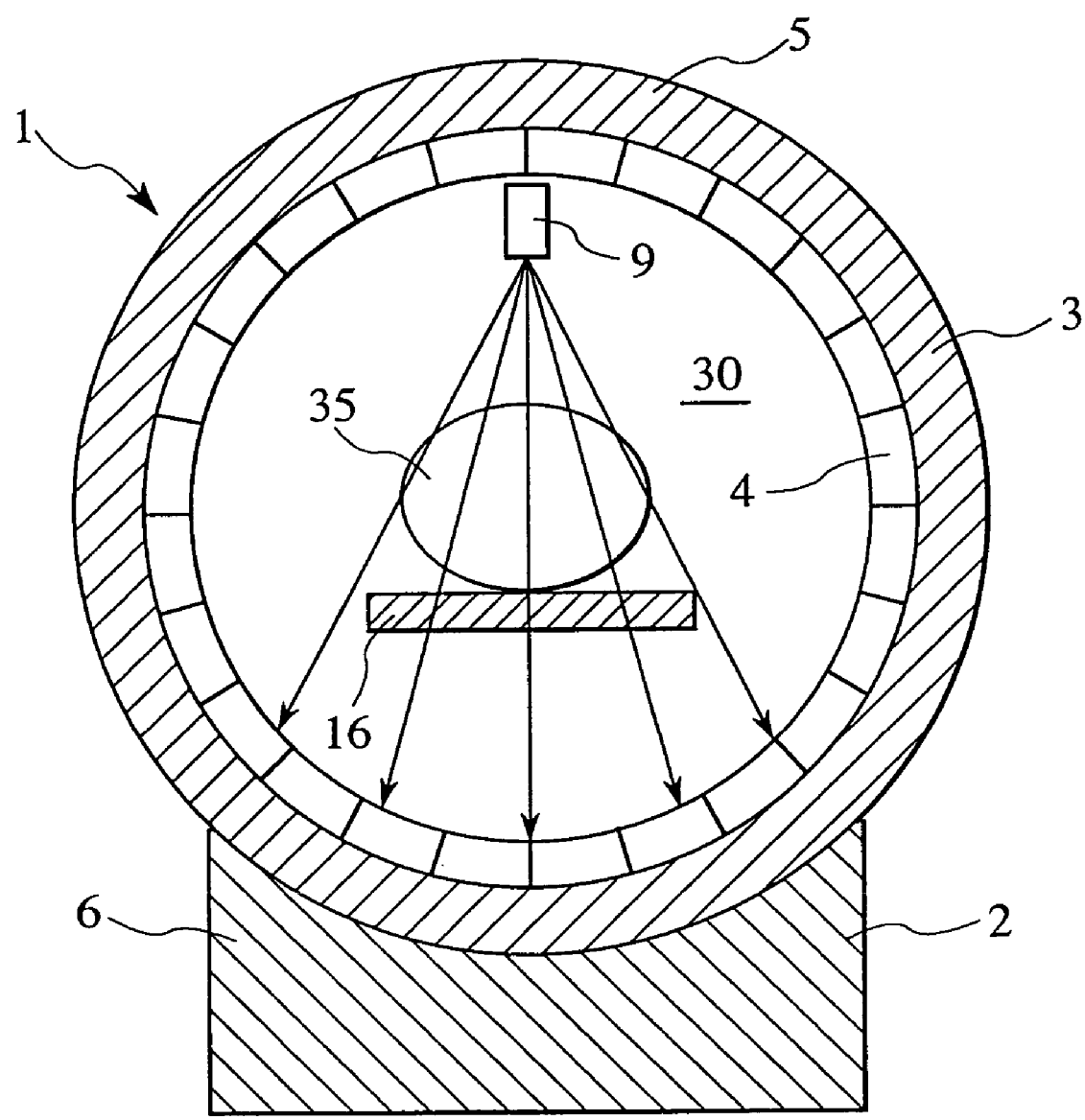
FIG. 3 is a cross-sectional view taken along line III–III of FIG. 2.

The radiation examining apparatus 1 will next be explained using FIGS. 1, 2 and 3. The radiation examining apparatus 1 includes an imaging device 2, an examinee holding device 14, a signal processing device or processor 37, a tomogram creating device 38 and a display device 29. The signal processor 37 has a signal discriminating device 19 and a simultaneous counting device 26. The tomogram creating device 38 has a computer 27 (e.g., work station) and a storage device 28. The examinee holding device 14 has a support member 15 and a bed 16 positioned at an upper end of the support member 15 and mounted to the support member 15 so as to be movable in its longitudinal direction.

The imaging device 2 is placed in a direction normal to the longitudinal direction of the bed 16 and has a radiation detector ring body 3, an X-ray source circumferential moving device 7, a drive device controller 17, an X-ray source controller 18, and a casing 36. The radiation detector ring body 3, the X-ray source circumferential moving device 7, the drive device controller 17 and the X-ray controller 18 are placed within the casing 36. The radiation detector ring body 3 includes a ring-shaped holder 5 and a large number of radiation detectors 4 circularly locate inside the ring-shaped holder 5. A penetrating through hole or opening portion 30 corresponding to an observation region through which the bed 16 is inserted, is defined inside the radiation detectors 4 of the radiation detector ring body 3. The large number of radiation detectors 4 (about 10000 in total) are placed within the ring-shaped holder 5 in plural form not only in its circumferential direction but also in an axial direction of the through hole section 30. Each of the radiation detectors 4 is a semiconductor radiation detector and has a 5-mm cubic semiconductor device unit used as a detection unit, which comprises cadmium telluride (CdTe). The semiconductor device unit may be comprised of gallium arsenide (GaAs) or cadmium zinc telluride (CZT). The ring-shaped holder 5 is placed on a support member 6. The support members 6 and 15 are installed to the floor of an examination room. The drive device controller 17 and the X-ray controller 18 are placed on the outer surface of the ring-shaped holder 5.

The X-ray circumferential moving device 7 is provided with an X-ray source device 8 and a ring X-ray source device holder 13. The X-ray source device holder 13 is attached to the outer surface of the ring-shaped holder 5 at one end thereof. A ring-shaped guide rail 12 is placed at one end face of the X-ray source device holder 13. The guide rail 12 and the X-ray source device holder 13 surround the periphery of the through hole section 30. The X-ray source device 8 has an X-ray source 9, an X-ray source drive device 10 and an axially-moving arm 11. Although not shown in the drawing, the X-ray source drive device 10 is provided with a first motor and a power transmission mechanism coupled to a ratatable shaft of the first motor within a casing thereof. The flexible axially-moving arm 11 is attached to the casing of the X-ray source drive device 10 and extends to within the through hole section 30. The X-ray source 9 is attached to the axially-moving arm 11. The axially-moving arm 11 is expanded and contracted according to the action of a second motor (not shown) placed in the X-ray source drive device 10. The X-ray source drive device 10 is mounted to the guide rail 12 so as not to fall and so as to be movable along the guide rail 12. Although not shown in the drawing, the X-ray drive device 10 has a pinion maintained in meshing engagement with a rack attached to the guide rail 12 to thereby receive a rotating force from the above-described power transmission mechanism.

The X-ray source 9 has an X-ray tube known to date although not illustrated in the drawing. The X-ray tube includes, within an external cylinder thereof, an anode, a cathode, a current source of the cathode, and a voltage source for applying the voltage between the anode and the cathode. The cathode thereof is a filament made up of tungsten. The current source causes a current to flow into the cathode to thereby emit electrons from the cathode. The electrons are accelerated under a voltage (several hundred of kV) applied between the cathode and the anode from the voltage source and collide with the anode (W, Mo or the like) corresponding to a target. Thus, X-rays of 80 keV are generated by the collision of the electrons with the anode and emitted from the X-ray source 9.

Figure 4:
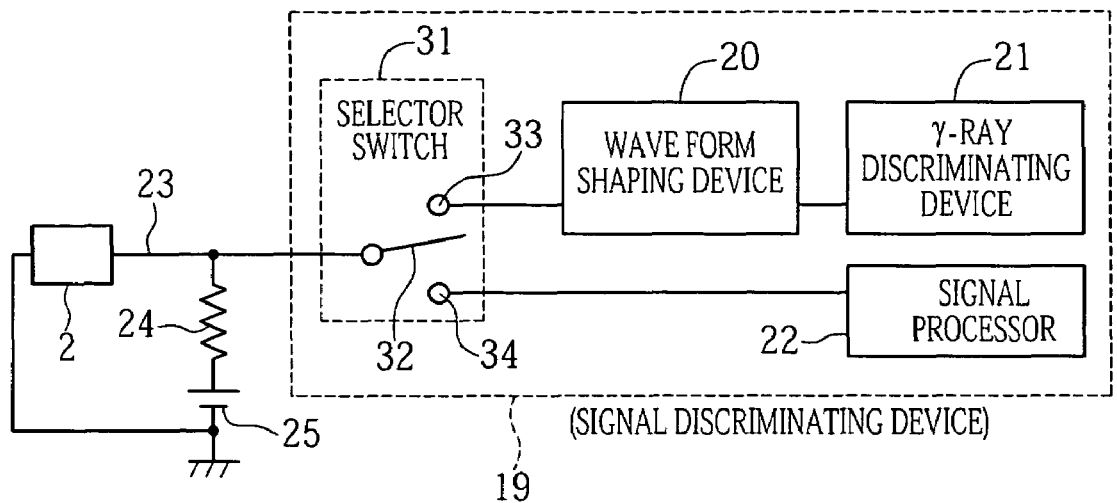
FIG. 4 is a detailed configurational view of a signal discriminating device shown in FIG. 2.

The respective radiation detectors 4 are respectively connected to their corresponding movable terminals 32 of the signal discriminating devices 19 by means of wires 23. One signal discriminating device 19 is provided for each radiation detector 4. A detailed configuration of the signal discriminating device is shown in FIG. 4. The signal discriminating device 19 includes a selector switch 31, a waveform shaping device or shaper 20, a γ-ray discriminating device or discriminator 21, and a signal processor 22 for determining an X-ray intensity. The selector switch 31 used as a switching device has a movable terminal 32 and fixed terminals 33 and 34. The waveform shaper 20 is connected to the fixed terminal 33 and the γ-ray discriminator 21. The signal processor 22 is connected to the fixed terminal 34. A power supply 25 is connected to its corresponding wire 23 and radiation detector 4. The γ-ray discriminator 21 is connected to the computer 27 via the simultaneous counting device 26. The simultaneous counting device 26 is provided as single and connected to all γ-ray discriminators 21. The respective signal processors 22 are connected to the computer 27. The storage device 28 and display device 29 are connected to the computer 27. The signal discriminating device 19 has an X-ray detect signal processor or processing device including the signal processor 22, and a γ-ray detect signal processor or processing device having the waveform shaper 20 and the γ-ray discriminator 21.

Prior to the description of the tomogram creating method according to the present embodiment, a radiographic examination using the radiation examining apparatuses 1 and 40 will be described. Prior to administration of a PET medical agent to the examinee 35, an X-ray CT examination using the radiation examining apparatus 40, which corresponds to the X-ray CT, is performed. The examinee 35 is laid on the bed 48 and inserted into the through hole section 46. The X-ray source 43 and the radiation detectors 44 are rotated while the examinee 35 is being irradiated with the X rays emitted from the X-ray source 43. The X rays transmitted through the examinee 35 are detected by the plurality of radiation detectors 44. Detect signals (hereinafter called "first X-ray detect signal") of the X rays outputted from the respective radiation detectors 44 are inputted to their corresponding signal processors 49. Each of the signal processing devices 49 obtains an X-ray intensity, based on the first X-ray detect signal and outputs X-ray intensity information to the computer 27. The X-ray CT examination using the radiation examining apparatus 40 is effected on an examination range identical to that for the PET examination using the radiation examining apparatus 1 and executed in a state (called a "breath-held state") in which the examinee 35 is being breath-held.

The radiation examination using the radiation examining apparatus 1 will next be explained. The radiation examining apparatus 1 performs the X-ray CT examination and the PET examination by means of one imaging device 2.

Prior to a specific description of the examination by the radiation examining apparatus 1, the principle of a radiation detection by the radiation examining apparatus 1 will be described. The present embodiment has been made by application of the following discussions made by the present inventors. Data about an X-ray CT image (tomogram, i.e., living-body structural image, which is created based on each X-ray detected signal obtained by the X-ray CT examination and includes images about inward organs and bones for a sample or specimen to be examined) is created by irradiating the specimen with the X rays emitted from the X-ray source in a specific direction for a predetermined period of time, and repeating the work (scan) of detecting the X rays transmitted through its body by the radiation detectors and by being based on the strengths of the X rays detected by the plurality of radiation detectors. It is desirable that in order to obtain data about an X-ray CT image good in accuracy, γ rays emitted from inside the specimen due to a PET medical agent are not launched into the corresponding X-ray detecting radiation detector upon the X-ray CT examination. To this end, the time required to irradiate the specimen with the X rays has been shortened based on novel findings of the inventors, that "if the time required to irradiate the specimen with the X rays is shortened in association with the rate of incidence of the γ rays, then one radiation detector is capable of neglecting the influence of the γ rays". Now consider the rate of launching of the γ rays into one radiation detector in order to determine the time T required to irradiate the specimen with the X rays. Assuming that radioactivity in the body based on the PET medical agent administrated to the specimen upon the PET examination is represented as N(Bq), the rate of penetration of the generated γ rays into the body is represented as A, an incident rate obtained from a solid angle of one radiation detector is represented as B, and the sensitivity of a detecting element is represented as C respectively, the rate α (rays/sec) of γ rays detected by one radiation detector is given by the following equation (1). "2" indicative of a coefficient in the equation (1) means that a pair of γ rays (two) is emitted upon extinction of one positron. A probability W that the γ rays will be detected by one detecting element within the irradiation time T is given by the following equation (2).

$$\alpha = 2NABC \quad (1)$$

$$W = 1 - \exp(-T\alpha) \quad (2)$$

By determining the irradiation time T so that the value of W in the equation (2) becomes small, the influence of the γ rays launched into one radiation detector is made nearly negligible upon the X-ray CT examination.

One example of the X-ray irradiation time T will be explained below. A specific X-ray irradiation time T was obtained based on the equations (1) and (2). The intensity of radiation in a body due to a radioactive medical agent administrated to a specimen to be examined, upon the PET examination is about 370 MBq at maximum (N=370 MBq). The in vivo penetration rate A of γ rays is about 0.6 (A=0.6) assuming that the body of the specimen is water whose radius is 15 cm. Now consider where for example, a radiation detector whose one side is 5 mm, is disposed in a ring form with a radius of 50 cm. In this case, the incident rate B obtained from a solid angle of one radiation detector is 8×10−6 (B=8×10−6). The sensitivity C of detection by the radiation detector is about 0.6 (C=0.6) at maximum where a semiconductor radiation detector is used. From these values, the rate α of detection of γ rays by one radiation detector is on the order of about 2000 (rays/sec). If the X-ray irradiation time T is 1.5 μsec, for example, then the probability W of detecting the γ rays by one radiation detector during the X-ray examination results in 0.003, and hence the γ rays can be substantially neglected. If the X-ray irradiation time is set to 1.5 μsec or less where the radioactivity to be administrated to the specimen is set to less than 360 MBq, then W<0.003, i.e., the probability of detection of the γ rays reaches 0.3% or less, which is negligible.

The X-ray CT examination and PET examination done by the radiation examining apparatus 1 to which the above-described principle is applied, will be specifically explained. First of all, the PET medical agent is administered to the examinee 35 corresponding to a specimen in such a manner that the in-vivo administered radioactivity reaches 370 MBq. The PET medical agent is selected according to examination purposes (such as grasping of a cancer's position or the examination of an arterial flow of the heart, etc.). After the PET medical agent is administrated thereto and a predetermined time has elapsed, the examinee 35 is laid on the bed 16 and inserted into the through hole section 30. The X-ray CT examination and PET examination by the radiation examining apparatus 1 are carried out using the imaging device 2 in this state.

The X-ray source controller 18 controls the time required to discharge or emit the X rays from the X-ray source 9. Namely, the X-ray source controller 18 repeats control for outputting an X-ray generation signal during the X-ray CT examination to thereby close a switch (hereinafter called an "X-ray source switch" which is not shown in the drawing) provided between the anode (or cathode) of the X-ray tube in the X-ray source 9 and the power supply, outputting an X-ray stop signal when a first set time has elapsed, to thereby open the X-ray source switch, and closing the X-ray source switch when a second set time has elapsed. The voltage is applied between the anode and cathode for the first set time, and no voltage is applied therebetween for the second set time. Owing to such control, the X rays are emitted from the X-ray tube in a pulse form. The irradiation time T corresponding to the first set time is set to, for example, 1 μsec so that the probability of detection of the γ rays by the corresponding radiation detector 4 is negligible. The second set time is a time T0 during which the X-ray source 9 is transferred or moved between one radiation detector 4 and other radiation detector 4 adjacent thereto in its circumferential direction, and is determined by a moving velocity of the X-ray source 9 in the circumferential direction of the guide rail 12. The first and second set times have already been stored in the X-ray source controller.

When the X-ray CT examination is started, the drive device controller 17 outputs a drive start signal to thereby close a switch (hereinafter called a "first motor switch") to be coupled to the power supply, which has been connected to the first motor of the X-ray source drive device 10. Owing to the supply of a current, the first motor is rotated and its rotating force is transmitted to the pinion via the power transmission mechanism, so that the pinion is rotated. According to the rotation of the pinion, the X-ray source device 8, i.e., the X-ray source 9 moves around the examinee 35 at a set velocity along the guide rail 12. Upon the completion of the X-ray CT examination, the drive device controller 17 outputs a drive stop signal to open the first motor switch. Consequently, the movement of the X-ray source 9 in the circumferential direction is stopped. In the present embodiment, all the radiation detectors 4 circularly disposed in the circumferential direction are neither shifted in the circumferential direction nor in the axial direction of the through hole section 30. The known technology no interfering with the movement of the X-ray source controller is applied to the transmission of the control signal from the non-moved X-ray source controller and drive device controller to the moved X-ray source device.

The drive start signal outputted form the drive device controller 17 when the X-ray CT examination is started, is inputted to the X-ray source controller 18. The X-ray source controller 18 outputs an X-ray generation signal, based on the input of the drive start signal. Thereafter, the X-ray source controller 18 repeatedly outputs the X-ray stop signal and the X-ray generation signal. According to the repeated output of the X-ray stop signal and X-ray generation signal, the X-ray source 9 emits X rays for the first set time (1 μsec) and stops the emission thereof for the second set time. The emission and stop of the X rays are repeated during the period in which the X-ray source 9 is moved in the circumferential direction. The X rays emitted from the X-ray source 9 are applied to the examinee 35 lying within the through hole section 30 in a fan-beam form. Owing to the movement of the X-ray source 9 in the circumferential direction, the examinee 35 on the bed 16 is irradiated with the X rays from its periphery. After the X rays have been transmitted through the examinee 35, they are detected by the plurality of radiation detectors 4 located in the circumferential direction with the radiation detector 4 placed in opposite directions at an angle of 180° from the X-ray source 9 being taken as the center with the axial center of the through hole section 30 as a base point or origin. These radiation detectors 4 output detected signals (hereinafter called "second X-ray detect signals") of the X rays. The second X-ray detect signal is inputted to its corresponding signal discriminating device 19 via the corresponding wire 23. Those radiation detectors 4 having detected the X rays are called "first radiation detectors 4" for convenience.

γ rays of 511 keV due to the PET medical agent are discharged or emitted from the examinee 35 lying within the through hole section 30. The radiation detectors 4 other than the first radiation detectors 4 detect the γ rays discharged from the examinee 35 and output detected signals (hereinafter called "γ-ray detect signals") of the γ rays. The γ-ray detect signals are inputted to their corresponding signal discriminating devices 19 via the corresponding wires 23. The radiation detectors 4 having detected the γ rays are referred to as "second radiation detectors 4" for convenience.

The X-ray CT examination and PET examination executed by the radiation examining apparatus 1 as described above are performed in a state (hereinafter called "breathed state") in which the examinee 35 is being breathed. Examination ranges for the examinee 35 at these examinations are identical. In the breathed state, body surfaces of a chest region and an abdominal region of the examinee 35 are swung like an arrow 62 indicated in FIG. 8B. When the examination ranges for the X-ray CT examination and PET examination are intended for a wide range like being intended for the whole body of the examinee 35, for example, the bed 16 is shifted so that the examination ranges for the examinee 35 fall within the through hole section 30, whereby these examinations are executed.

The γ-ray detect signal outputted from the corresponding second radiation detector 4 is transferred to its corresponding γ-ray discriminator 21 within the signal discriminating device 19, whereas the second X-ray detect signal outputted from the corresponding first radiation detector 4 is transmitted to its corresponding signal processor 22. The transmission of such respective detect signals is done according to a switching operation of the selector switch 31 of the signal discriminating device 19. The switching operation for connecting the movable terminal 32 of the selector switch 31 to the fixed terminal 33 or 34 is performed based on a switching control signal corresponding to the output of the drive device controller 17. The drive device controller 17 controls the shifting operation of the X-ray source device 10 as described above and simultaneously selects the corresponding first radiation detector 4 and connects the movable terminal 32 of the selector switch 31 in the signal discriminating device 19 connected to the first radiation detector 4 to its corresponding fixed terminal 34.

The selection of the first radiation detector 4 will be explained. An encoder (not shown) is coupled to the first motor lying within the X-ray source drive device 10. The drive device controller 17 receives therein a signal detected by the encoder to determine the position of the X-ray source drive device 10, i.e., the X-ray source 9 in the circumferential direction and select the corresponding radiation detector 4 located 180° opposite to the position of the X-ray source 9 by using stored data about the positions of the respective radiation detectors 4. Since the X rays emitted from the X-ray source 9 have a certain width as viewed in the circumferential direction of the guide rail 12, the radiation detectors 4 for detecting the X rays having penetrated into the body of the examinee 35 exist in the circumferential direction in plural form in addition to the selected radiation detector 4. The drive device controller 17 selects the plurality of radiation detectors 4 too. These radiation detectors 4 correspond to the first radiation detectors. With the movement of the X-ray source 9 in the circumferential direction, the corresponding first radiation detector 4 is made different too. With the shift of the X-ray source 9 in the circumferential direction, the first radiation detectors 4 look as if being shifted in the circumferential direction on a pseudo basis. When the drive device controller 17 has selected another radiation detector 4 with the movement of the X-ray source 9 in the circumferential direction, the corresponding movable terminal 32 connected to the radiation detector 4 corresponding to the first radiation detector 4 is newly connected to its corresponding fixed terminal 34. The corresponding movable terminal 32 connected to its radiation detector 4 out of the first radiation detector 4 with the movement of the X-ray source 9 in the circumferential direction is connected to its corresponding fixed terminal 33 by means of the drive device controller 17.

It can be also said that each of the first radiation detectors 4 is of the radiation detector 4 connected to the signal processor 22 by the selector switch 31. It can be also said that each of the second radiation detectors 4 is of the radiation detector 4 connected to the γ-ray discriminating device 21 by the selector switch 31. Each individual radiation detector 4 installed to the ring-shaped holder 5 serves as the first radiation detector 4 on one occasion from the relationship with the position of the X-ray source 9 and serves as the second radiation detector 4 on another occasion. Therefore, one radiation detector 4 outputs both the second X-ray detect signal and γ-ray detect signal while they are shifted on a time basis and discrete.

Each of the first radiation detectors 4 detects the X rays applied from the X-ray source 9 for 1 μsec corresponding to the first set time and transmitted through the examinee 35. The probability that the first radiation detector 4 will detect the γ rays discharged from the examinee 35 for 1 μsec, is as small as negligible as described above. The large number of γ rays generated within the body of the examinee 35 due to the PET medical agent are emitted in all directions without being emitted in a specific direction. These γ rays are emitted in nearly direct opposite directions (at 180°±0.6°) as pairs and detected by any of the second radiation detectors 4 in the radiation detector ring body 3.

A description will be made of signal processing of the signal discriminating device 19 at the time that the second X-ray detect signal and γ-ray detect signal outputted from the radiation detector 4. The second X-ray detect signal outputted from the first radiation detector 4 is inputted to its corresponding signal processor 22 under the action of the selector switch 31 as described above. The signal processor 22 determines the intensity of the second X-ray detect signal, based on the input second X-ray detect signal and outputs its intensity information therefrom.

Figure 5:
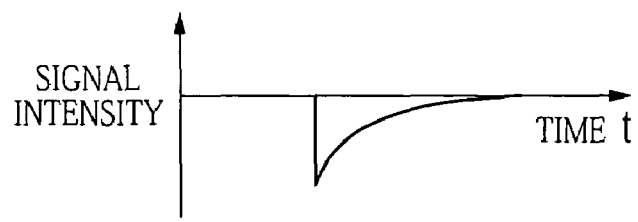
FIG. 5 is an explanatory-view showing a waveform of a γ-ray detect signal inputted to a waveform shaper shown in FIG. 4.
Figure 6:
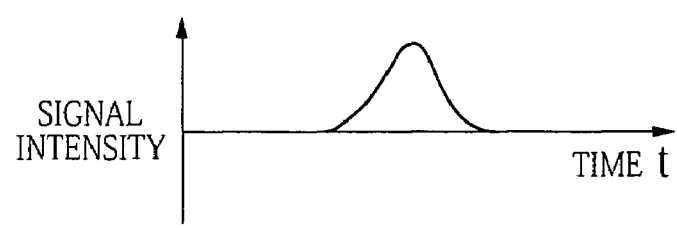
FIG. 6 is an explanatory view illustrating a waveform of a γ-ray detect signal outputted from the waveform shaper shown in FIG. 4.

The γ-ray detect signal outputted from the second radiation detector 4 is inputted to its corresponding waveform shaper 20 under the action of the selector switch 31. The γ-ray detect signal inputted to the waveform shaper 20 is brought to such a shape as to suddenly fall at first and thereafter exponentially reach 0 as shown in FIG. 5. The γ-ray discriminating device 21 inputted with an output signal of the waveform shaper 20 is not capable of processing the γ-ray detect signal having such a waveform as shown in FIG. 5. Therefore, the waveform shaper 20 converts the γ-ray detect signal having such a waveform as shown in FIG. 5 into a γ-ray detect signal having such a temporal waveform of Gaussian distribution as shown in FIG. 6 by way of example and outputs it therefrom. The energy of the γ rays generated within the body due to the extinction of positrons emitted from the PET medical agent is given as 511 keV as mentioned previously. However, all of the energy of γ rays are not necessarily converted into electrical charges within a semiconductor device section. Therefore, the γ-ray discriminating device 21 sets 450 keV lower than the energy of 511 keV as an energy set value, for example and generates a pulse signal having predetermined energy when an imaging signal having energy greater than the energy set value (called a "first energy set value") is inputted thereto. Namely, the γ-ray discriminating device 21 is a device for generating the pulse signal having the above energy when the imaging signal (γ-ray detect signal) having the energy greater than the first energy set value.

In order to allow the γ-ray discriminating device 21 to process the γ-ray detect signal having specific energy as described above, a filter for allowing an imaging signal lying within a predetermined energy range to pass therethrough may be provided within the γ-ray discriminating device 21 (or at a stage prior to the γ-ray discriminating device 21). The γ-ray discriminating device 21 generates a pulse signal in response to the imaging signal transmitted through the first filter.

The simultaneous counting devices 26 receive pulse signals outputted from their corresponding γ-ray discriminating devices 21 of the respective signal discriminating devices 19, and perform simultaneous counting every γ rays using these pulse signals to thereby determine counted values for γ-ray detect signals. Further, each of the simultaneous counting devices 26 brings two detection points (equivalent to positions of one pair of the radiation detectors 4 different in direction by nearly 180° (strictly 180°±0.6°) with the axial center of the through hole section 30 as the center) at which the respective γ rays of each γ-ray pair are detected according to one pair of pulse signals for the γ-ray pair, into data form as position information about γ-ray detection.

A description will be made of a process of creating tomograms by the tomogram creating device 38. Respective tomograms for a specimen, which have been created based on the X-ray detect signals outputted from the radiation detectors 4 and 44, are referred to as "X-ray CT images". The X-ray CT images are tomograms containing images about inward organs and bones for the specimen, i.e., living-body structural images. On the other hand, a tomogram for the specimen, which has been created based on the γ-ray detect signal outputted from each of the radiation detectors 4, is called a "PET image". The PET image is of a tomogram including a region (e.g., an affected part) in the specimen, on which a radioactive medical agent is concentrated, i.e., a living-body functional image. The tomogram creating device 38 reconstructs an X-ray CT image (hereinafter called a "first X-ray CT image") based on the first X-ray detect signal outputted from the radiation detector 44, reconstructs an X-ray CT image (hereinafter called a "second X-ray CT image") based on a second X-ray detect signal outputted from the radiation detector 4, and reconstructs a PET image, based on the γ-ray detect signal outputted from the radiation detector 4. Further, the tomogram creating device 38 corrects data about the PET image, based on the degree of distortion of the second X-ray CT image based on the second X-ray detect signal detected in a breathed state relative to the first X-ray CT image obtained based on the first X-ray detect signal detected in an unbreathed state. According to the above processing of the tomogram creating device 38, the PET image data (called "corrected PET image data") in the unbreathed state can be created from the PET image data obtained based on the γ-ray detect signal in the breathed state.

Figure 7:
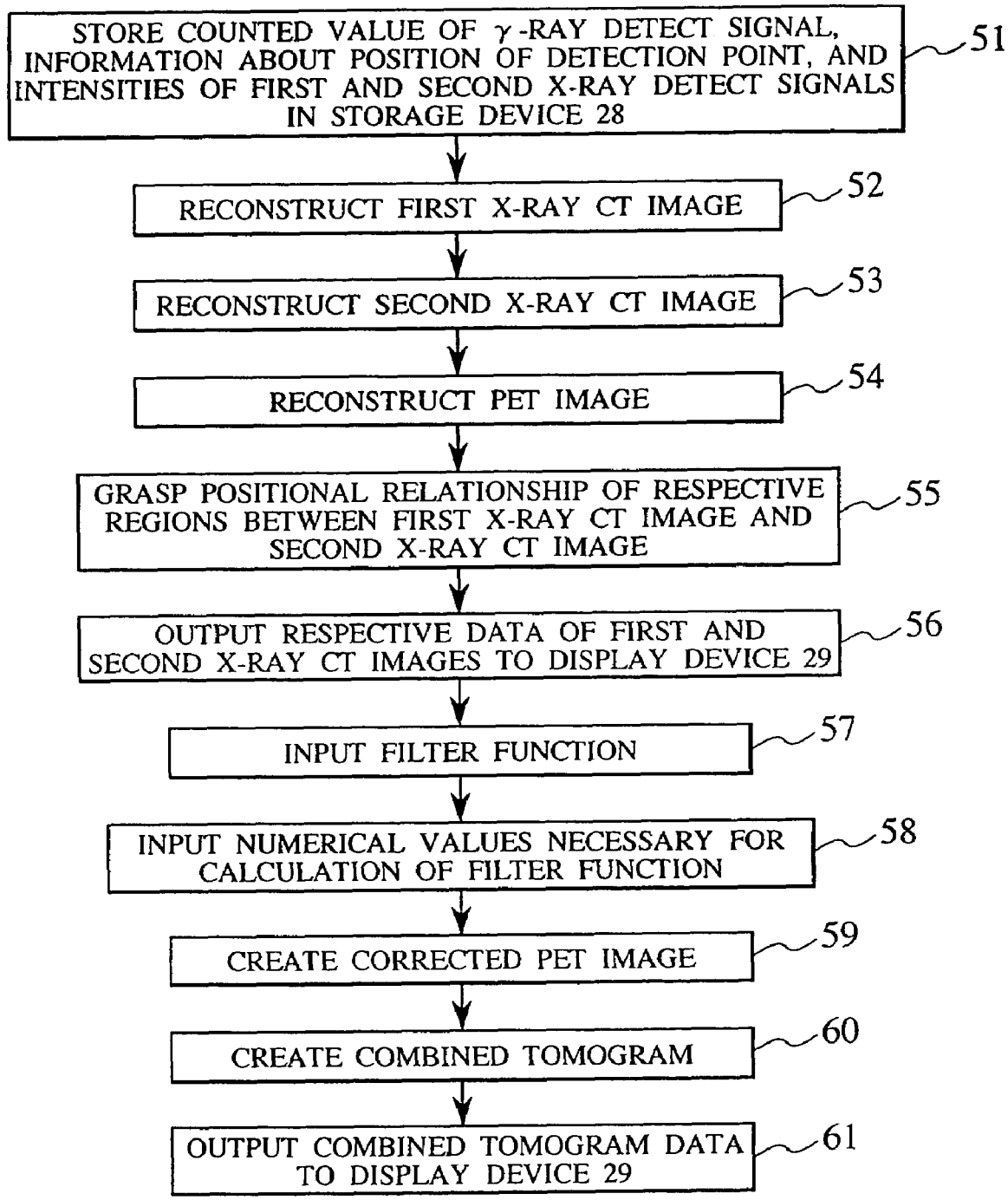
FIG. 7 is a flowchart for describing a tomogram creating process executed by a computer shown in FIG. 2.

A process of reconstructing tomograms by the tomogram creating device 38 will be specifically explained. The computer 27 executes the tomogram reconstructing process, based on a processing procedure of Steps 51 through 61 shown in FIG. 7. The computer 27 receives a value of a γ-ray detect signal, which is counted by the simultaneous counting device 26, information about the position of each detected point, which is outputted from the simultaneous counting device 26, the intensity of a second X-ray detect signal outputted from the signal processor 22, and the intensity of a first X-ray detect signal outputted from the signal processing device 49 and stores them in the storage device 28 (Step 51). The computer 27 reconstructs a first X-ray CT image indicative of a tomogram for a specimen or examinee 35, using the intensity of the first X-ray detect signal stored in the storage device 28 (Step 52). Data (about a first X-ray CT image shown in a lattice section of FIG. 8A by way of example) about the created first X-ray CT image is stored in the storage device 28. The computer 27 reconstructs a second X-ray CT image indicative of a tomogram for the examinee 35, using the intensity of the second X-ray detect signal stored in the storage device 28 (Step 53). Data about the created second X-ray CT image (second X-ray CT image shown in a lattice section of FIG. 8B by way of example) is stored in the storage device 28. The reconstruction of the respective X-ray CT images in Steps 52 and 53 is carried out by the Filtered Back Projection Method described in the aforementioned IEEE Transaction On Nuclear Science, Vol. NS-21, pp. 228–229. Next, the computer 27 reconstructs a PET image indicative of a tomogram for the examinee 35, using the counted value of the γ-ray detect signal and the information about the position of each detected point (Step 54). Date about the created PET image is stored in the storage device 28. The reconstruction of a PET image at the execution of two-dimensional imaging upon the PET examination may use the Filtered Back Projection method. The reconstruction of a PET image at the execution of three-dimensional imaging upon the PET examination may use a Fourier rebinning method described in, for example, 1997 IEEE Transaction On Medical Imaging, Vol. 16, pp 145. The order of executing the respective processes in Steps 52 through 54 may be started from any location.

Next, global alignment between respective regions at the first X-ray CT image in the unbreathed state and the second X-ray CT image in the breathed state is performed (Step 55). The global alignment described herein means that relatively large regions or portions in the body, such as a body surface, bones, etc. are brought into alignment with each other. Several regions such as the backbone, lung, body surface, etc., which exit in common in both images and are apt to be compared and which are relatively large in the body, are selected upon the global alignment. The selected regions are brought into global alignment within both the images.

One example of a method of performing the global alignment will be described below. When a human being is breathed, the size of its lung field varies and hence its cubic content changes. Individual differences exist in the direction and distance of traveling of it body surface at that time. When the body surface of the examinee 35 is moved in the direction indicated by the arrow 62 in FIG. 8B in a breathed state, for example, the selected common regions in the first X-ray CT image and the second X-ray CT image are not matched upon their movements, rotation and scaling. Therefore, the common regions selected in both images are brought into registration using, for example, deformable models to bring the selected common regions into global alignment. As one example of the global alignment using each deformable model, free-form deformations discussed in the IEEE Transaction On Medical Imaging Vol. 18, pp 712 is used. This technique is a method of representing large motion of the whole examinee by using affine transformation (transformation by rotation, parallel motion and scaling), and of using a deformable model using a beta spline function in the motion of part of the lung field or the like in each image.

The computer 27 outputs respective data about the first X-ray CT image and the second X-ray CT image to the display device 29 (Step 56). The first X-ray CT image shown in FIG. 8A and the second X-ray CT image shown in FIG. 8B are displayed on the display device 29. Next, the computer 27 inputs filter functions thereto (Step 57). An operator looks at their tomograms displayed on the display device 29 and selects a filter function necessary to create a correction PET image. Since the alignment is done using the deformable models in Step 55, the operator is able to grasp to a degree how the regions move at the respective potions. If the first X-ray CT image and the second X-ray CT image coincide with each other globally and locally, then a function indicative of the used deformable models results in the corresponding filter function upon selection of the data filter function. However, even if the global alignment is done, their inconsistent regions exist when the images are seen locally. The operator selects a suitable filter function for them from within a plurality of the filter functions displayed on the display device 29. The computer 27 takes in or captures the plurality of filter functions stored in the storage device 28 and outputs them to the display device 29 to thereby perform the display of the plurality of filter functions on the display device 29. The selected filter function is inputted to within the computer 27. When no suitable filter function exists in the displayed filter functions, the operator inputs a suitable filter function to the computer 27 by using an input device (e.g., a keyboard).

The filter function is correction information indicative of an image positional relationship, which is used to correct image blurring (distortion) of the second X-ray CT image aligned with the first X-ray CT image with respect to the first X-ray CT image. According to the global alignment process in Step 55, local displacements of organs or the like are modeled and corrected by using deformable models in both the first X-ray CT image and the second X-ray CT image aligned with the first X-ray CT image. Therefore, barycentric positions of bones and organs and the size of a body surface, and the like are made coincident. However, in the second X-ray CT image corresponding to the tomogram in the breathed state, images of regions swung by breathing or the like are blurred because of their swinging. Therefore, an idea was taken that the image of each blurred region in the second X-ray CT image was corrected to thereby bring it to an image of a non-blurred region, like the first X-ray CT image. The filter function is used to make a correction of the image of each blurred region in the second X-ray CT image to the image of the non-blurred region.

Let's assume that, for example, a region identical in the second X-ray CT image of FIG. 8B to a region represented by a circle 63A in the swing-free first X-ray CT image shown in FIG. 8A is expressed in an ellipse 63B due to its local swing. In this case, the region brought to the ellipse 63B is corrected using a filter function for setting the ellipse 63B to the circle 63A, so that the shape of the region expressed in the ellipse 63B in the second X-ray CT image can be corrected to the circle. On the other hand, when a region identical to a region represented as a circle 64A in the first X-ray CT image (see FIG. 8A) is expressed in a circle 64B in a manner similar to the above even in the case of the second X-ray CT image (see FIG. 8B), the region expressed in the circle 64B in the second X-ray CT image is not affected by the swing indicated by the arrow 62. Therefore, the local correction of the region by the corresponding filter function is unnecessary. Accordingly, the filter function for the region coincides with the function of the previously-used deformable model. When the function of the ellipse 63B is expressed in the following equation (3) and the function of the circle 63A is expressed in the following equation (4), a filter function f corresponding to a correction coefficient, for making a correction of the ellipse 63B to the circle 63A is expressed in the following equation (5). r indicates the radius of the circle, a indicates the major axis of the ellipse, and b indicates the minor axis thereof, respectively.

$$(x-x_1)^2/a^2+(y-y_1)^2 b^2=1 \quad (3)$$

$$(x-x_2)^2/r^2+(y-y_2)^2/r^2 1 \quad (4)$$

$$f(x,y)=(r(x-x_1)/a-_2,r(y-y_2)/b+y_2) \quad (5)$$

Numerical values necessary for the calculation of filter functions are inputted to the computer 27 (Step 58). The operator inputs the numerical values necessary for the calculation of the corresponding filter while looking at the first X-ray CT image and second X-ray CT image displayed on the display device 29. The operator reads the numerical values of r, a and b in the filter function of the equation (5) from the respective CT images displayed on the display device 29 and inputs them, for example.

The PET image in the breathed state, which has been obtained in Step 54, is corrected (Step 59). Correcting the PET image in the breathed state makes it possible to obtain a PET image in an unbreathed state. Upon this correction, the numerical values inputted in Step 58 are substituted in the corresponding filter function (e.g., filter function f). The PET image in the breathed state is corrected using the obtained filter function. Since the PET image and the second X-ray CT image are reconstructed using the γ-ray detect signal and second X-ray detect signal detected in the breathed state of the examinee 35, the condition of blurring of an image based on the breathing of the examinee 35 is the same. Thus, the blurred PET image is corrected by the image reconstructed in Step 54, using the value-substituted filter function to thereby make it possible to create a corrected PET image whose blurring has been solved. Creating the corrected PET image makes it possible to obtain a PET image good in accuracy, in which the blurred portion has been reduced significantly.

The corrected PET image and X-ray CT image are combined together to create a combined tomogram (Step 60). The combined tomogram is created by combining the corrected PET image and the first X-ray CT image. In the radiation examining apparatus 1, both a second X-ray detect signal and a γ-ray detect signal are outputted from the corresponding radiation detector 4. A second X-ray CT image created based on the second X-ray detect signal, and a PET image created based on the γ-ray detect signal are coincident with each other in the position of the axial center of the through hole section 30. Since the second X-ray CT image and the first X-ray CT image are of living-body structural images, regions (e.g., backbones) free from swinging even in the breathed state are brought into alignment to enable the shifting of the position of the axial center of the through hole section 30 in the second X-ray CT image to the first X-ray CT image. Since the corrected PET image is obtained by correcting the PET image created in Step 54, both PET images are coincident with each other in the position of the axial center of the through hole section 30. Thus, the corrected PET image and the first X-ray CT image can be combined together easily and with satisfactory accuracy by allowing the positions of the axial centers of the through hole sections 30 to coincide with each other, thereby making it possible to create a combined tomogram containing living-body structural images and living-body functional images. Data about the combined tomogram is outputted to the display device 29 (Step 61). The combined-tomogram data is displayed on the display device 29.

After Step 54, the second X-ray CT image and the PET image created in Step 54 are combined together with the axial center of the through hole section 30 as the basis to thereby create a combined tomogram, and the processes of Steps 55 through 58 are executed. Afterwards, the process of the correction effected on the PET image in Step 59 may be effected on the combined tomogram containing the second X-ray CT image and the PET image. Consequently, the combined tomogram from which the blurring in the breathed state has been solved, can be obtained. Since the correcting process is effected even on the second X-ray CT image in the present embodiment, the processing time required to create the combined tomogram from which the blurring has been solved, becomes long as compared with the aforementioned embodiment.

According to the present embodiment, advantageous effects shown below can be obtained.

(1) Since a PET image blurred under the influence of the swing of a body due to breathing is corrected based on correction information indicative of an image positional relationship between a first X-ray CT image unblurred under uninfluence of the swing of the body due to the breathing, and a second X-ray CT image blurred under the influence of its swing, a PET image from which the influence of the swing due to the breathing is eliminated, can be obtained. Since the correction using the correction information indicative of the image positional information as described above is carried out in the present embodiment, the PET image can be corrected with satisfactory accuracy as compared with the correction based on the information about the body movements of the examinee, which has been detected by the sensor described in Japanese Patent No. 3022773. This is because the conditions of the swings at the individual regions in the body can be grasped based on the first X-ray CT image and second X-ray CT image and reflected on the correction in the present embodiment, whereas the swings of the individual regions in the body cannot be grasped accurately from the body-motion information detected by the sensor. Therefore, the present embodiment is capable of effecting accurate diagnosis on the regions on which the PET medical agent is concentrated within the body of the examinee 35, as compared with Japanese Patent No. 3022773.

(2) There is no need to newly provide a sensor for detecting breath-based swings. An X-ray CT installed in a hospital or the like is used as the radiation examining apparatus 40, and an X-ray detect signal outputted from its corresponding radiation detector of the X-ray CT may be used as a first X-ray detect signal. Incidentally, when the X-ray CT is installed in other hospital, it may cause the tomogram creating device 38 to transmit the resultant first X-ray detect signal through the use of communication lines such as Internet, etc.

(3) In the present embodiment, the radiation detectors 4 disposed in circular form are capable of detecting both γ rays emitted due to a PET medical agent from the examinee 35 corresponding to a specimen, and X rays irradiated from the X-ray source 9 moved in a circumferential direction and transmitted through the examinee 35. Therefore, while the prior art has needed, as imaging devices, an imaging device for detecting transmitted X rays, and other imaging device for detecting γ rays, the present embodiment may be provided with one imaging device, and a radiation examining apparatus capable of executing both an X-ray CT examination and a PET examination can be simplified in configuration.

(4) In the present embodiment, each of the radiation detectors 4 disposed in circular form is capable of detecting both a second X-ray detect signal corresponding to a detected signal of X rays transmitted through the body of the examinee 35, and a γ-ray detect signal corresponding to a detected signal of γ rays discharged from the body due to a radioactive medical agent. Such a configuration also contributes to further simplification of the configuration of the radiation examining apparatus, and scale-down thereof.

(5) In the present embodiment, a second X-ray CT image including images of inward organs and bones of the examinee 35 can be reconstructed using a second X-ray detect signal corresponding to an output signal from one of the radiation detectors 4 disposed in circular form. A PET image including an image of a region (e.g., an affected part of a cancer) in the examinee 35, on which a radioactive medical agent is concentrated, can be reconstructed using a γ-ray detect signal corresponding to an output signal of other radiation detector 4 for outputting the second X-ray detect signal. Since data about the second X-ray CT image and data about the PET image are reconstructed based on the second X-ray detect signal and γ-ray detect signal outputted from their corresponding radiation detectors 4, data about a first X-ray tomogram and data about a corrected PET image, which are not under the influence of a swing due to breathing, can be combined together while being aligned with satisfactory accuracy. It is therefore possible to easily obtain a tomogram (combined tomogram) containing the image of the region with the PET medical agent concentrated thereon, and the images of the inward organs and bones. According to the combined tomogram, the position of each affected part can be accurately recognized according to the relationship between the inward organs and bones. For example, data about a first tomogram and data about a second tomogram are brought into alignment with the axial center of the through hole section 30 of the imaging device 2 as the center, whereby image data in which both tomograms are combined together, can be easily obtained.

(6) Since an imaging signal necessary to create the first tomogram and an imaging signal necessary to create the second tomogram can be obtained from the shared radiation detector 4 in the present embodiment, the time (examination time) required to inspect the examinee 35 can be significantly shortened. In other words, the imaging signal necessary to create the first tomogram and the imaging signal necessary to create the second tomogram can be obtained in a short period of examination time. The present embodiment needs not to shift the examinee from an imaging device for detecting transmitted X rays to another imaging device for detecting γ rays as in the case of the prior art. Thus, the probability that the examinee will move, can be reduced. Avoidance of the necessity of shifting the examinee from the imaging device for detecting the transmitted X rays to other imaging device for detecting the γ rays also contributes to shortening of the time required to inspect the examinee.

(7) Since the X-ray source 9 is circumferentially rotated and the radiation detector ring body 3, i.e., the radiation detectors 4 are not shifted in the circumferential and axial directions of the through hole section 30 in the present embodiment, the capacity of a motor for allowing the X-ray source 9 to go or orbit around can be reduced as compared with a motor necessary for shifting the radiation detector ring body 3. Power consumption required to drive the latter motor can be reduced as compared with the former motor.

(8) Since the γ-ray detect signal inputted to the signal processor 22, i.e., a first signal processor is significantly reduced, data about a first tomogram good in accuracy can be obtained. It is therefore possible to more accurately recognize the position of a patient owing to the use of image data obtained by combining the data about the first tomogram and data about a second tomogram together.

(9) Since the X-ray source 9 goes around inside the radiation detectors 4 disposed in circular form, the diameter of the ring-shaped holder 5 becomes large, and the number of the radiation detectors 4 installable inside the ring-shaped holder 5 in the circumferential direction can be increased. The increase in the number of the radiation detectors 4 in the circumferential direction will yield an improvement in sensitivity and improve resolution of a transverse section of the examinee 35.

(10) Since the axially-moving arm 11 with the X-ray source 9 attached thereto and the X-ray source 9 are disposed inside the radiation detectors 4 in the present embodiment, there is a possibility that they will block out or shield the γ rays emitted from the examinee 35 to disable the detection of the γ rays by the radiation detector 4 located just at the back thereof, thus suffering a loss of detection data necessary to create a PET image. Since, however, the X-ray source 9 and the axially-moving arm 11 are turned in the circumferential direction by the X-ray source drive device 10 as described above in the present embodiment, the loss of the data substantially presents no problem. In particular, the orbiting velocity of the X-ray source 9 and axially-moving arm 11 is about 1 sec/1 slice, and is sufficiently shorter than the time of the order of a few minutes at shortest necessary for the PET examination. Even in this case, the loss of the data substantially presents no problem. When no X-ray CT examination is done, the devices related to the X-ray CT examination are withdrawn or taken out from within the radiation detectors 4 and stored. For example, the X-ray source 9 is stored in the X-ray source drive device 10 in the present embodiment.

Second Embodiment

Figure 9:
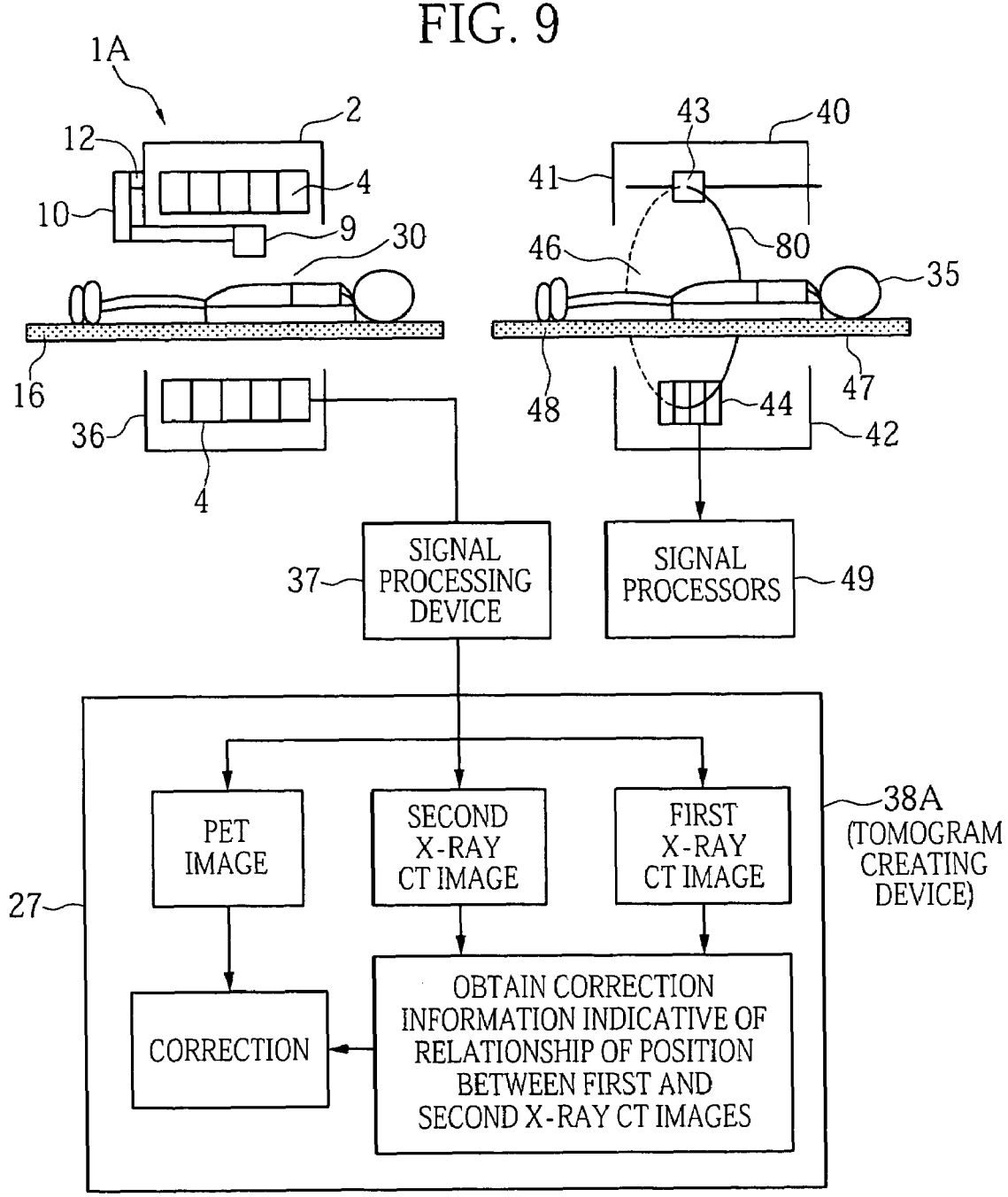
FIG. 9 is a configurational view of a radiation examining apparatus used in a tomogram creating method of a second embodiment, which shows another embodiment of the present invention.

A method of creating tomograms, which shows another embodiment of the present invention, will be explained using FIG. 9. A radiation examining apparatus 1A is used in the tomogram creating method showing the present embodiment. The radiation examining apparatus 1A has a configuration wherein the tomogram creating device 38 of the radiation examining apparatus 1 is replaced by a tomogram creating device 38A. The radiation examining apparatus 1A is identical in other configuration to the radiation examining apparatus 1. The tomogram creating device 38A receives a first X-ray detect signal from its corresponding radiation detector 4.

In the present embodiment, an X-ray CT examination in an unbreathed state is done using the radiation examining apparatus 1A. Namely, an examinee 35 to which no PET medical agent is administered, is placed on a bed 16 and inserted into a through hole or opening portion 30. An X-ray source 9 is turned around the periphery of the examinee 35 by using an X-ray source drive device 10 to irradiate the unbreathed examinee 35 with X rays emitted from the X-ray source 9, whereby the X-ray CT examination in the unbreathed state is performed. Upon the X-ray CT examination in the unbreathed state, the corresponding radiation detector 4 outputs the first X-ray detect signal. A signal processor 22 of a signal discriminating device 19 receives the first X-ray detect signal therein and outputs a signal indicative of the intensity of the first X-ray detect signal to the tomogram creating device 38A. The tomogram creating device 38A executes the respective processes of Steps 51 through 61 shown in FIG. 7 to thereby create a combined tomogram and displays data of the combined tomogram on a display device 29.

The present embodiment is capable of obtaining the advantageous effects (1) through (10) brought about in the first embodiment. Further, the present embodiment needs not to perform the X-ray CT examination in the unbreathed state by using another radiation examining apparatus 40 and is capable of performing it using the radiation examining apparatus 1A used in the execution of an X-ray CT examination in a breathed state.

Third Embodiment

Figure 10:
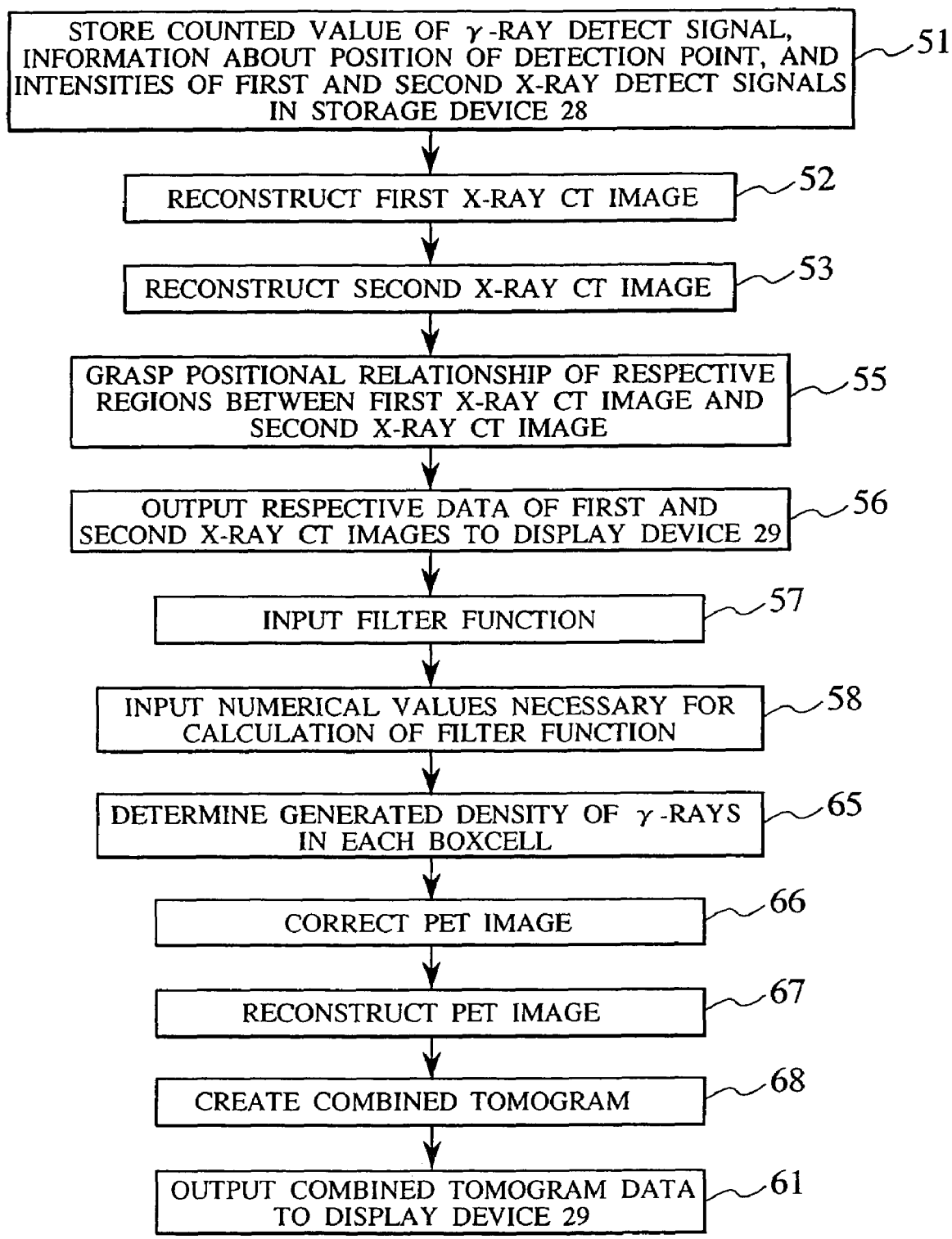
FIG. 10 is a flowchart for describing a tomogram creating process executed by a computer of a radiation examining system used in a tomogram creating method of a third embodiment, which shows a further embodiment of the present invention.

A tomogram creating method showing a further embodiment of the present invention will be explained. The radiation examining apparatuses 1 and 40 shown in FIG. 1 are used in the present embodiment. A tomogram creating device 38 employed in the present embodiment executes respective processes of Steps 51 through 53, 55 through 58, 65 through 68 and 61 shown in FIG. 10.

In a manner similar to the first embodiment, the radiation examining apparatus 40 is used to effect an X-ray CT examination on an examinee 35 in an unbreathed state. The intensity of a first X-ray detect signal outputted from the corresponding radiation detector 44 is determined by a signal processing device 49, which in turn is inputted to a computer 27. An X-ray CT examination and a PET examination in a breathed state are executed using the radiation examining apparatus 1 in a manner similar to the first embodiment. However, the X-ray CT examination in the breathed state is performed in a short period of time (e.g., in one second or so). Therefore, a swing with breathing, of a body of the examinee 35 for the short period of time becomes very small. Information about the intensity of a second X-ray detect signal outputted from a signal processor 22, a counted value of a γ-ray detect signal outputted from a simultaneous counting device 26, and the position of each detection point are inputted to the computer 27. In a manner similar to the first embodiment, the computer 27 performs the processes of Steps 51 through 53. Since a second X-ray CT image reconstructed in Step 53 in the present embodiment is less subjected to the influence of the breath-based swing because the X-ray CT examination is done in the short period of time as described above. Further, the processes of Steps 55 through 58 are executed.

The generated density of each γ-ray pair in each voxel in the body is determined (Step 65). The generated density of each γ-ray pair for each voxel existing between a pair of radiation detectors 4 having detected respective γ rays of each γ-ray pair is determined based on the information about the counted value of the γ-ray detect signal and the position of each detection point. The generated density of each γ-ray pair is determined with respect to each voxel existing between the pair of radiation detectors 4 for each γ-ray pair.

Figures 11A, 11B:
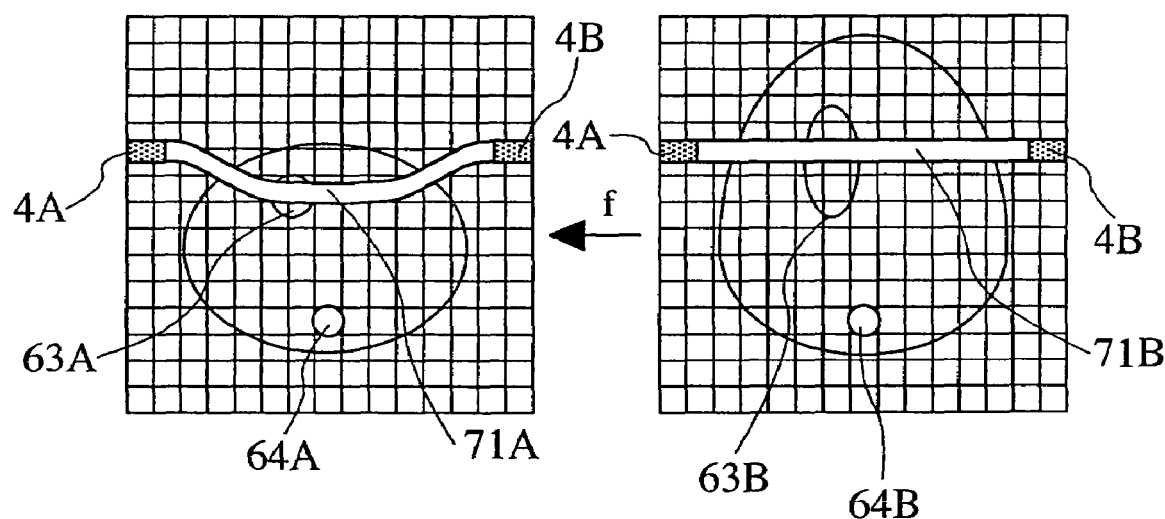
FIG. 11A is an explanatory view showing a first X-ray CT image obtained based on an X-ray detect signal obtained by an X-ray CT examination in an unbreathed state, which has been executed using the radiation examining apparatus 40.
FIG. 11B is an explanatory view showing a second X-ray CT image obtained based on an X-ray detect signal obtained by an X-ray CT examination in a breathed state, which has been executed using the radiation examining apparatus 1.

PET data is corrected using a filter function in which the resultant alignment exchange information and numerical values are substituted (Step 66). Namely, the positions of the respective voxels are corrected using the filter function in which the alignment exchange information and numerical values are substituted. The correction for the PET data will be explained using FIG. 11. For example, FIG. 11A shows a first X-ray CT image created based on a first X-ray detect signal obtained by an X-ray CT examination using the radiation examining apparatus 40 at a given time. FIG. 11B illustrates a second X-ray CT image created based on a second X-ray detect signal obtained by an X-ray CT examination using the radiation examining apparatus 1 at a given time. Now consider where respective γ rays of each γ-ray pair obtained by a PET examination using the radiation examining apparatus 1 at that time are detected by a pair of radiation detectors 4A and 4B. At this time, a γ-ray pair is generated within a region 71B (FIG. 11B) lying between the pair of radiation detector 4A and 4B. The positions of respective voxels in the region 71B are corrected using a filter function in which alignment exchange information and numerical values are substituted. Owing to this correction, the position (corrected position) of each voxel in a state unaffected by a breath-based swing is determined. The corrected position of each voxel is represented like a region 71A shown in FIG. 11A. The filter function with the numerical values substituted therein is used to calculate corrected positions of voxels in an ellipse 63B. The corrected positions of such voxels are determined for all γ-ray pairs. The positions of each voxel and the generated density of each γ-ray pair at the voxel are voxel information. The correction of the position of each voxel by the filter function with the alignment exchange information and numerical values substituted therein means that the voxel information is corrected based on correction information.

Afterwards, the PET image is reconstructed (Step 67). The PET image is reconstructed by using the information about the corrected positions of the respective voxels and the generated density of each γ-ray pair with respect to the voxels. The reconstructed PET image results in one from which the influence of the breath-based swing has been eliminated. The reconstruction of the PET image is performed by a reconstruction method using a repetition method described in, for example, Medical Imaging Technology, No. 1 in Vol. 18, pp 40–45. The PET image and the first X-ray CT image are combined together to create a combined tomogram (Step 68). According to Step 61, data about the combined tomogram is displayed on a display device 29.

Incidentally, when it is difficult to always perform the X-ray CT examination during the PET examination, an X-ray CT examination capable of detecting a second X-ray detect signal necessary to reconstruct a second X-ray CT image, for example, is carried out during one cycle of the breath of the examinee 35, and in which state of the previously-imaged second X-ray CT image the body is placed, is measured using a marker, whereby a correction function at each time may be calculated from the corresponding second X-ray CT image.

The present embodiment is capable of obtaining the advantageous effects (1) through (10) produced in the first embodiment. Further, since the present embodiment reconstructs the PET image by using the PET data in which the position of each voxel has been corrected, the time required to detect the second X-ray detect signal is short as compared with the first embodiment, and a finer PET image from which the influence of the breath-based swing has been eliminated, can be obtained. Since the X-ray CT examination using the radiation examining apparatus 1 is performed over a long hours in the first embodiment, a problem arises in that the correction becomes inaccurate as the examination time becomes long. The present embodiment is capable of solving such a problem.

In the third embodiment, the second X-ray detect signal may be obtained from the corresponding radiation detector 4 of the radiation examining apparatus 1 without using the radiation examining apparatus 40 in a manner similar to the second embodiment.

While the first through third embodiments described above are intended for PET, the tomogram creating devices and tomogram creating methods according to these embodiments are applicable even to a case in which a SPECT examination and an X-ray CT examination are executed in radiation examining apparatuses 1 and 1B. In this case, collimators for specifying the directions of incidence of γ rays to respective radiation detectors are installed inside radiation detector groups of both the radiation examining apparatuses 1 and 1B.

According to the present invention, owing to corrections using respective data about a first structural tomogram obtained based on a first radiation detect signal in an unbreathed state and a second structural tomogram obtained based on a second radiation detect signal in a breathed state, a tomogram for radiation discharged traceable from a specimen can be obtained in which the influence of a breath-based swing is less reduced. Therefore, the accuracy of a diagnosis effected on a region on which a radioactive medical agent is concentrated, is improved.

While the invention has been described in its preferred embodiments, it is to be understood that the words which have been used are words of description rather than limitation and that changes within the purview of the appended claims may be made without departing from the true scope and spirit of the invention in its broader aspects.

What is claimed is:

1. A tomogram creating method, comprising the following steps:
   acquiring first radiation signals, while a body to be examined ceases breathing, with respect to radiation transmitted through the body;
   a first structural tomogram creating step for creating data to be used for constructing a first structural tomogram, based on said first radiation signals;
   acquiring second radiation signals, while the body to be examined is breathing, with respect to radiation transmitted through the body;
   a second structural tomogram creating step for creating data to be used for constructing a second structural tomogram, based on said second radiation signals;

a correction information creating step for creating correction information to be used for correcting image blurring of said second structural tomogram with respect to said first structural tomogram, based on the data to be used for constructing said first and second structural tomograms;

acquiring third radiation signals, while the body to be examined is breathing, with respect to radiation emitted from the body to be examined due to a radioactive medical agent; and a functional tomogram creating step of creating a functional tomogram, based on said third radiation signals and the correction information.

2. The tomogram creating method according to claim 1, wherein the first radiation signals and the second radiation signals are detect signals outputted from discrete radiation examining apparatuses each of which detects the radiation emitted from a radiation source and transmitted through the body.

3. The tomogram creating method according to claim 1, wherein the second radiation signals and the third radiation signals are detect signals outputted from radiation detectors of a radiation examining apparatus used in both a second examination for irradiating the body with second radiation from a radiation source and detecting the same, and a third examination for detecting third radiation emitted from the body due to a radioactive medical agent.

4. The tomogram creating method according to claim 1, wherein the first radiation signals are signals outputted from radiation detectors of a radiation examining apparatus used in a first examination for irradiating the body while the body ceases breathing with first radiation from a radiation source and detecting the same.

5. The tomogram creating method according to any of claims 1 to 4, wherein the functional tomogram creating step has a step for creating data about a first functional tomogram, based on the third radiation signals and a step for creating data about a second functional tomogram obtained by correcting the first functional tomogram data by the correction information.

6. The tomogram creating method according to any of claims 1 to 4, wherein the functional tomogram creating step includes a step for creating voxel information in the body, based on the third radiation signals, and a step for creating data about the functional tomogram, based on the voxel information corrected by the correction information.

* * * * *